(12) United States Patent
Brintrup Meeder

(10) Patent No.: US 10,905,147 B2
(45) Date of Patent: Feb. 2, 2021

(54) PROCESS FOR THE PREPARATION OF AN ADDITIVE AS A FOOD SUPPLEMENT BASED ON SEAWEEDS FOR BIRDS AND ANIMALS; AS WELL AS THE PRODUCT OBTAINED AND ITS USE IN THE FOOD CONVERSION AND IN THE PRODUCTION OF BIRD AND ANIMAL MEAT

(71) Applicant: Patagonia Biotecnología S.A., Santiago (CL)

(72) Inventor: Marcelo Brintrup Meeder, Puerto Varas (CL)

(73) Assignee: PATAGONIA BIOTECNOLOGÍA S.A., Santiago (CL)

( * ) Notice: Subject to any disclaimer, the term of this patent is extended or adjusted under 35 U.S.C. 154(b) by 219 days.

(21) Appl. No.: 15/857,542

(22) Filed: Dec. 28, 2017

(65) Prior Publication Data

US 2018/0184699 A1 Jul. 5, 2018

(30) Foreign Application Priority Data

Dec. 30, 2016 (CL) .................................. 3431-2016

(51) Int. Cl.
| | |
|---|---|
| *A23L 33/105* | (2016.01) |
| *A23K 10/30* | (2016.01) |
| *A23K 20/10* | (2016.01) |
| *A23L 17/60* | (2016.01) |
| *A23L 33/19* | (2016.01) |
| *A23L 33/115* | (2016.01) |
| *A23L 33/16* | (2016.01) |
| *A61K 36/02* | (2006.01) |

(52) U.S. Cl.
CPC ............ *A23L 33/105* (2016.08); *A23K 10/30* (2016.05); *A23K 20/10* (2016.05); *A23L 17/60* (2016.08); *A23L 33/115* (2016.08); *A23L 33/16* (2016.08); *A23L 33/19* (2016.08); *A61K 36/02* (2013.01); *A23V 2002/00* (2013.01); *A23V 2200/26* (2013.01); *A23V 2250/1576* (2013.01); *A23V 2250/16* (2013.01); *A23V 2250/1638* (2013.01); *A23V 2250/21* (2013.01); *A23V 2250/54252* (2013.01); *A23V 2250/6408* (2013.01); *A23V 2300/10* (2013.01); *A23V 2300/24* (2013.01); *A23V 2300/38* (2013.01)

(58) Field of Classification Search
CPC ........ A23L 33/105; A23L 17/60; A23L 33/19; A23L 33/115; A23L 33/16; A23K 10/30; A23K 20/10; A61K 36/02
See application file for complete search history.

(56) References Cited

U.S. PATENT DOCUMENTS

| | | | |
|---|---|---|---|
| 2004/0144144 A1 | 6/2004 | De La Fuente Jimenez et al. | |
| 2004/0157932 A1* | 8/2004 | Saebo ................... | A23K 20/105 514/625 |
| 2005/0023217 A1* | 2/2005 | Grech ....................... | C02F 1/50 210/610 |
| 2005/0100622 A1* | 5/2005 | Nair ...................... | A61K 36/185 424/777 |
| 2006/0088574 A1* | 4/2006 | Manning ................. | A23L 33/40 424/439 |
| 2015/0351408 A1* | 12/2015 | Meeder ................... | A01N 65/03 504/117 |
| 2017/0209471 A1* | 7/2017 | Widberg ................. | A23L 33/00 |

FOREIGN PATENT DOCUMENTS

| | | |
|---|---|---|
| ES | 2193893 A1 | 11/2003 |
| FR | 3012293 A1 | 5/2015 |
| WO | 9700017 A1 | 1/1997 |
| WO | 2011063817 A3 | 6/2011 |
| WO | 2014068601 A1 | 5/2014 |

OTHER PUBLICATIONS

Saurabh Bhatia et al. Avicenna Journal of Phytomedicine, vol. 5(1) pp. 69-77, Jan.-Feb. 2015 (Year: 2015).*
"Technique: Tangy Yogurt Cream Cheese and whey" downloaded from https://www.organicspark.com/portfolio/ypgurt_cream_cheese_whey/ 12 pages dated Mar. 2010. (Year: 2010).*
Machine translation of CN 102488253 dated 2012 (Year: 2012).*
Kulshreshtha et al., "Feed Supplementation with Red Seaweeds, Chondrus crispus and Sarcondiotheca gaudichaudii, reduce *Salmonella enteritidis* in Laying Hens", frontiers in Microbiology, Apr. 10, 2017, vol. 8, 12 pages.
Rey-Crespo et al., "The use of seaweed from the Galician coast as a mineral supplement in organic dairy cattle", Animal (2014), 8:4, 7 pages.
Official Certificate and English Translation thereof for Chilean Patent Application No. 1464-2014 issued on Jun. 4, 2014, 51 pages.

* cited by examiner

*Primary Examiner* — C. Sayala
(74) *Attorney, Agent, or Firm* — Hoffman Warnick LLC

(57) ABSTRACT

The present invention relates to a process for preparing an additive as a food supplement based on algae for birds and animals. It also describes the food additive obtained, formulated with seaweed extract, whey, malto-dextrin, proteins, amino acids, minerals, fiber, fat, hormones, and has a final powder form. In addition, the use of the food additive to increase the weight gain in animals, the weight gain in eggs of birds, and for the production of meat in birds and animals is described.

13 Claims, No Drawings

PROCESS FOR THE PREPARATION OF AN ADDITIVE AS A FOOD SUPPLEMENT BASED ON SEAWEEDS FOR BIRDS AND ANIMALS; AS WELL AS THE PRODUCT OBTAINED AND ITS USE IN THE FOOD CONVERSION AND IN THE PRODUCTION OF BIRD AND ANIMAL MEAT

FIELD OF APPLICATION

In general terms, the present invention refers to a process for the preparation of an additive as a food supplement for birds and animals, as well as such additive in powder form formulated from seaweed extracts.

BACKGROUND OF THE INVENTION

Several methods to obtain food supplements for animals are known in the state of the art.

Among these, and related with the present invention, we found document WO2011063817 A3, describing a food supplement comprising a mechanical regulator of satiety selected from at least one plant fiber or seaweed fiber from the group comprised of galactomannan, glucomannan, pectin, arabinoxilane, cellulose, alginate y/o chitosan; a chemical inductor of satiety selected from a protease inhibitor; a thermogenic selected from plant extract from different species; an at least one side effects remover from different plan species, preferably, from mint plants.

Additionally, it is mentioned that among the options for a satiety chemical inductor, it can be milk serum and it is described that the alginate is extracted from *Macrocystis pyrifera*.

Another related disclosure is document WO 2014068601, teaching a process to produce a protein hydrolyzed from aquatic organisms, comprising the addition of a natural antioxidant from seaweed, before or during the hydrolysis reaction. Seaweed can be selected from *Macrocystis pyrifera*. The process comprises the stages of grinding the protein source in the presence of water; recovering the ground pulp and adjusting the protein content to a range between 0.1-30% w/v; adjusting the pH and temperature; performing the enzymatic hydrolysis between 0.1-48 hours until reaching a hydrolysis degree between 2-70% and to stop the hydrolysis reaction deactivating the enzyme by pH or temperature. Then the hydrolyzed aquatic peptide is separated from the solid fraction by means of ultrafiltration using specific size membranes and by means of centrifugation; the solid fraction is dried. It also claimed the product obtained from it and its use in the manufacture of food supplements and meals, among other options.

Document US20040144144 A1 describes a productive process to manufacture a grow stimulant for organic plants from seaweed comprising: receiving the raw materials from previously washed with salt water *Macrocystis pyrifera* and *Ulva rigida*; grinding *Ulva* until it has a size to about 0.2 mm; weighting *Macrocystis* and *Ulva* in a proportion of *Macrocystis:Ulva* from 1:1 to 10:1; washing *Macrocystis* with sweet water; slicing *Macrocystis* to a size of 1 cm; treating with HCl the sliced *Macrocystis* for about 30-40 minutes at a 50° C. temperature, producing alginic acid; draining the algae; washing it with water; grinding to a size of 0.4 cm; digesting with $K_2CO_3$, mixing it in this stage with *Ulva* ground in the previous stage, controlling pH to about 10 and temperature at about 65±5° C. for 2 hours; adding an acid to reduce the pH to 4.5-6.2; filtering; and packaging the liquid product. The biostimulant product obtained has a high concentration of mineral elements, amino acids, vitamins and phytohormones such as auxins and cytokines.

Document CL1464-2014 describes a process to manufacture a biostimulant based on seaweed comprising the stages of selection and grinding of the fresh seaweed; wash of the seaweed; acid treatment of the seaweed with acetic acid; alkaline treatment of the product with KOH; separation and recovery of the liquid phase and addition of hydrolyzed leonardita americana; and dried until obtaining a powder.

Document ES2193893 describes a process of manufacture food for aquiculture for seaweed flour biotransformation characterized by the stages of moisturizing, decalcification and acid attack; enzymatic treatment with carbohydrases; transformation of the polysaccharides obtained in the biomass and degradation of the cell walls of the seaweeds; and deactivation of the product to conserve it during several months.

Document WO9700017 A1 describes a nutritional supplement comprising 25-75% in weight of the selected seaweed from the genre *Macrocystis*, 10-50% in weight of yeast, y 10-30% in weight of the minerals selected from calcite.

Document FR3012293A1 describes a food ingredient comprising seaweed extract from *Laminaria japonica* and has in its composition 10-60% in weight of sodium minerals; 1-10% in weight of potassium; 2-20% in weight of glutamate; 0.1-10% in weight of iodine. The seaweed extract represents between 20-90% in weight of the ingredient, which can be selected from brown seaweeds (*Laminaria japonica*), and red seaweed (*Gracilaria* spp., and *Porphyra* spp.) or combinations thereof. Additionally it can comprise saccharides selected from starch, hydrolyzed starch or oligosaccharides, present between 10-80% in weight of the final ingredient. Claim 13 describes a process for the ingredient preparation, comprising the seaweed extraction; seaweed extract concentration in the previous step to yield a concentrated extract and dry the product. Furthermore, it mentions that the seaweed concentrated extract can be mixed with a saccharide before drying.

The non-patent document "*Feed supplementation with red seaweeds, Chondrus crispus and Sarcodiotheca gaudichaudii, affects performance, egg quality, and gut microbiota of layer hens*" wrote by G. Kulshreshtha, 2014, describes a study where adding extracts from red seaweed *Chondrus crispus* and *Sarcodioheca gaudichaudii* in the bird's diet, resulting in an improvement in the production of eggs.

Non-patent document "*The use of seaweed from the Galician coast as a mineral supplement in organic dairy cattle*" wrote by F. Rey-Crespo, 2014, describes the use of seaweed as a mineral supplement in the daily diet of livestock, specifically seaweed selected from *Ulva rigida*, *Sargasum muticum*, and *Saccorhiza polyschides*. Results showed that seaweed supplementation in the livestock food significantly improved iodine and selenium in blood and excreted in the milk produced by the animals.

Nevertheless, none of the documents known in the state of that describes a process to prepare an additive as a dietary supplement in birds and animals to increase the weight gain of the live animal and increase the weight of eggs in birds, wherein said obtained additive is formulated based on seaweed extract, milk serum, maltodextrin, proteins, amino acids, minerals, fiber, fat and hormones, and powder as final format that facilitates the transport and allows to extend its lifetime.

DESCRIPTION OF THE INVENTION

The present invention it refers to a process to manufacture an additive as a dietary supplement for birds and animals, such as said powder dietary supplement, formulated based on seaweed extract, whey, malto-dextrin, proteins, amino acids, minerals, fiber, fat, and hormones, and have a final format of powder. The main stages of said process are described as follows:

a. Selecting and washing the seaweeds;
b. Grinding the seaweed;
c. Adding hot water, including vapor;
d. Acid treatment of the seaweed;
e. Washing the seaweed after the acid treatments of step d) and incubate with water;
f. adding whey during the water incubation period from step e);
g. applying the alkaline treatment with constant agitation;
h. adding the hydrolyzed starch during the seaweed hydrolysis period of step g);
i. filtering to separate the solid phase from the liquid phase;
j. concentrating the liquid phase under vacuum;
k. drying, until the powder product is obtained;
l. finally packing and storing the obtained product.

DETAILED DESCRIPTION OF THE INVENTION

The process described in the present invention allows manufacturing an additive as a dietary supplement in birds and animals. Below, the foundations of each of the process steps are described:

Selection and Washing of Seaweed:

Artisanal fisherman collected fresh seaweed from the coast of the town of Niebla, in Valdivia, Región de los Rios. Transfer to the plant was carried out by a closed truck. Once collected, seaweed must be washed before to the grinding stage.

Grinding of the Seaweed:

Seaweed trituration is done to facilitate salt removal and acid treatment, besides reaching a particle size that allows the chemical reactives to uniformly penetrate the seaweed, producing more homogeneous reactions, and therefore, better control of the supplement composition. This is performed using a grinder, screw and/or knives mill, to reach a more uniform particle size, in the range of 0.5 and 1 cm.

Washing of Seaweed:

To remove mineral salts, excess seawater, sand, small mollusks, etc. from the seaweed, washes with hot water and steam are done.

Acid Treatment of the Seaweed:

Acid treatment of the seaweed is performed to remove the mineral salts and soluble organic materials remaining from the previous wash, as well as the sediments and organisms associated with the algae. Additionally, this treatment favors the chemical reaction for the ionic exchange between calcium, magnesium, and strontium ions present in the algae as an alginate of the corresponding divalent metal, producing algínico acid (HAlg). Apple vinegar is used in this stage, and then acetic acid is applied. Once the time for the acid treatment is finished, washing and incubation of the algae in water is performed to remove all the content of acid.

Addition of Whey:

Whey is added to the liquid resulting from the acid treatment in order to obtain a denser product.

Alkaline Treatment:

This stage is performed using potassium carbonate ($K_2CO_3$) applying temperature and constant agitation. This treatment is to neutralize the alginic acid contained in the algae particles with a potassium alkali, producing in this case soluble potassium alginate in aqueous solution, producing a viscous solution (400-600 Cps) with insoluble millimetric cellulose filaments.

Addition of the Hydrolyzed Starch:

Hydrolyzed starch was added to the liquid resulting from the alkaline treatment in order to obtain a denser product.

Filtration of the Product:

In this stage the insoluble cellulose particles remaining from the digestion are removed in order to clarify the alkaline extract solution. The size of the filter pore is equivalent to a final net size of 50, i.e., 250 microns. Afterwards the liquid phase undergoes a concentration under vacuum in order to concentrate the macronutrients present in the product.

Drying the Product:

This stage has the objective to dry the product by fast water evaporation, transforming the final product into a powder. This final format facilitates the transport, and storage, and also favors the product preservation, maintaining the biological properties of its macronutrients. Finally, the obtained product is packed and stored.

The product obtained by the described process has the following formulation:

6 to 10% in weight of proteins;

1 to 4% of fat;

8 to 12% in weight of whey;

4 to 6% in weight of hydrolyzed starch;

1 to 4% of glutamic acid;

25 to 30% of minerals;

5 to 8% of potassium carbonate;

14 to 18% of fiber; and

Natural Seaweed hormones.

The supplement obtained with this process has unique nutrient characteristics because of the algae extract, wherein the drying process used optimized the active ingredient and the beneficious components, as it is performed at controlled temperatures that maintain them intact, yielding an impalpable powder containing the most important active ingredients, and significantly reducing the volume and weight. These characteristics have important benefits:

a. It allows concentrating the nutritious elements of interest, increasing the bioavailability and a natural and specific character needed to a proper animal nutrition.

b. To omit the elements that do not provide nutrition to the animal. These residual elements make up most of the current products (up to 85% of the product in volume in some food based on seaweed flour, as they keep a high content of insoluble cellulose).

c. To significantly reduce the weight and volume, providing great benefits to the production, distribution, logistic and storage. The tests performed up to date in atomized productive processes, show that it is possible to reduce a product in liquid state (such as seaweed extract) with a volume of about 1000 $cm^3$ to a solid and dry product having a mass of only 30 g, and with a volume that makes possible to reduce the selling format up to a 15% of the original volume.

Periodic application of this dietary supplement favors the nutrition and health of birds and animals, being able to improve food conversion, bring forward the slaughter time and improve the meat quality in animals and increase the weight of the eggs in birds, producing a positive impact in the raising of birds and animals.

EXAMPLES

Example No 1 Process for the Manufacture of the Dietary Supplement a. Artisanal fisherman collected fresh seaweed from the coast of the town of Niebla, in Valdivia, Región de los Rios. Transferred to the plant was carried out by a closed truck. Once collected, seaweed must be washed previous to the grinding stage. Seaweed was selected from genres *Durvillaea* sp., *Macrocystis* sp., *Porphira* sp., *Ulva* sp., or combinations thereof. 1.000 kg of seaweed were weighted and washed were performed every 30 minutes in a liquid:solid ratio of 2:1 to extract salts and impurities from the fresh algae;

b. Seaweed was grinded using a grinder, screw and/or knives mill to obtain a particle size in the range between 0.5 and 1 cm;

c. For every 1,000 kg of initial seaweed, 2,000 L of hot water with steam inclusion was added, mixed in a tank with a 5.000 L capacity;

d. An acid treatment of the seaweed was performed, using between 50 to 70 L of apple vinegar for every 1,000 kg of the initial algae. Then between 50 to 70 L of acetic acid were added per 1,000 kg of initial seaweed. Acid treatment was performed at a pH between 2 and 6.5;

e. The seaweed was washed after the acid treatment of step d) and they were incubated in water tubs at a temperature between 45-65° C. for 90 to 120 minutes;

f. 90 to 108 kg of whey were added for every 1,000 kg of initial seaweed, during the water incubation stage in step e);

g. Alkaline treatment was performed applying between 45-50 kg of $K_2CO_3$ for every 1,000 kg of initial seaweed and was incubated at 70-85° C. during 120-150 minutes, with constant agitation. Alkaline treatment happened at a pH between 8.5 and 14;

h. 50 to 54 kg of hydrolyzed starch were added for every 1,000 kg of initial seaweed, during the algae hydrolysis stage in step g);

i. The product obtained from the alkaline treatment and the hydrolyzed starch addition was filtered to separate the solid phase from the liquid phase, using 250 microns filter paper;

j. Then, the liquid phase was concentrated under vacuum;

k. The product obtained was dried until the powder product was yielded by spray drying at an inlet temperature of 170° C. and an outlet temperature of 80° C.

l. Finally the product obtained was packed and stored.

Example No 2: Seaweed Analysis

Protein value from 4 different seaweed were studied and their results are shown in table No 1.

TABLE N° 1

Protein value from 4 species of seaweed collected from the Chilean coast

| Species | Net Protein (%) |
| --- | --- |
| *Porphyra columbina* | 21.32 |
| *Macrocystis pyrifera* | 8.77 |

TABLE N° 1-continued

Protein value from 4 species of seaweed collected from the Chilean coast

| Species | Net Protein (%) |
| --- | --- |
| *Ulva Lactuca* | 8.75 |
| *Durvillaea Antarctica* | 12.63 |

Example No 2 Dietary Supplement Analysis

Laboratory analysis was performed to the product obtained by the process described in example 1 in order to establish its formulation. The results are summarized in table No 3. The amino acidic balance from the dietary supplement is summarized in table 4, and the hormonal balance is summarized in table No 5.

TABLE N° 2

Composition of dietary supplement from the present invention.

| Dietary Supplement sample 100% Dried mass | Unit | Dry |
| --- | --- | --- |
| Total ashes | % | 27.98 |
| Net protein | % | 8.4 |
| Etheric extract | % | 0 |
| Raw fiber | % | 18 |
| Metabolizable energy | Mcal/K | 2.44 |
| Detergent fiber NE | % | 9.29 |
| Detergent fiber AC | % | 16.93 |
| Calcium | % | 0.71 |
| Cooper | Mcal/K | 66.42 |
| Iron | Mcal/K | 738.65 |
| Phosphorus | % | 0.263 |
| Manganese | Mcal/K | 13.28 |
| Magnesium | % | 0.463 |
| Potassium | % | 6.619 |
| Sodium | % | 2.277 |
| Zinc | Mcal/K | 21.25 |
| D Value | % | 66.4 |

TABLE N° 3

Amino acidic balance for the dietary supplement of the present invention.

| Amino acid | amino acid g/100 g proteins |
| --- | --- |
| Aspartic acid | 9.69 |
| Glutamic acid | 12.94 |
| Serine | 5.35 |
| Glycine | 4.11 |
| Histidine | 1.32 |
| Arginine | 5.01 |
| Tyrosine | 3.62 |
| Alanine | 7.72 |
| Proline | 6.12 |
| Tryptophan | 8.03 |
| Valine | 5.71 |
| Methionine | 1.83 |
| Cysteine | 2.39 |
| Isoleucine | 5.4 |
| Leucine | 8.79 |
| Phenylalanine | 4.4 |
| Lysine | 7.53 |

TABLE N° 4

Hormonal balance of the dietary supplement.

| Hormone | Amount (mgL$^{-1}$) |
|---|---|
| Gibberellins | 27.2 |
| Auxins | 0.23 |
| Cytokinins | 6.99 |
| Abcisic acid | 0.05 |

Example No 4 Feeding and Weighting of the Pigs 16 mixed breed pigs were selected (breed phenotypical influence from Large White), from about 65 days of age, kept in a semi-extensive system, with prior feeding based on whey, barley marc, wheat bran and concentrated. Pigs were weighted, ear tagged, treated for parasites (Invectina 1%) and batched in 3 homogenous groups. A pre-experimental period of 12 days for the new diet adaptation was considered (500 g de concentrated/day+serum ad libitum). Dietary supplement inclusion was initiated (20 g/day), plus 900 g/day of concentrated and 4.5 L of serum/day.

Weekly individual weighting were performed to evaluate the effect of the diet in the growth of pig. Based on the available data from weight measurements, analysis was performed to differentiate the additive effect on pigs. Table No 5 shows that from the 6th evaluation the weight difference is significant, reaching a difference of 6.7% in the mean weight between treatments, in measurement No 10.

TABLE N° 5

Mean live weight (kg) of the studied group in each weight.

| Weighing N° | Control Group (kg) | Treatment Group (kg) | % difference | p-value |
|---|---|---|---|---|
| 1 | 20.9 | 20.6 | −1.4 | |
| 2 | 29.7 | 29.2 | −1.5 | 0.926 |
| 3 | 32.6 | 32.7 | 0.3 | 0.378 |
| 4 | 35.9 | 36.1 | 0.7 | 0.361 |
| 5 | 40.3 | 41.5 | 3.0 | 0.144 |
| 6 | 42.4 | 44.2 | 4.2 | 0.040* |
| 7 | 46.0 | 48.1 | 4.6 | 0.056 |
| 10 | 53.3 | 56.8 | 6.7 | 0.027* |

*P-value for t-test to test significant difference (P < 0.05) between the means of the control and treatment group.

Example No 5: Quail Feeding and Egg Weighing 48 female quails distributed in 8 compartments, with 6 quails in each compartment were used. To improve the comfort of the birds in the study and provide a better management, the production room was provided with a heater to maintain and adequate temperature during the day. Feeding was of 35 g per bird, offering the food once a day, besides providing fresh water ad libitum for its consumption. Eggs were collected daily in 24 units plastic trays, which were weighted and labeled based on the group they are coming from (Group 1: non-supplemented diet; group 2: supplemented diet). Later, they were stored under refrigeration for evaluation. Table No 6 shows the average weight of the trays with 24 units of eggs and the average daily egg laying of quails fed with and without the seaweed supplement.

TABLE N° 6

Weight of the trays with 24 units of eggs from quails fed with and without the supplement.

| | Treatment | | |
|---|---|---|---|
| Variable | No supplement (group 1) | With Supplement (group 2) | P-value |
| Weight in grams of tray with 24 eggs/day | 246.3 | 262.3 | <0.0001 |
| Egg laying/day | 18.0 | 12.7 | <0.0001 |

Afterward, an exchange of diet phase was performed where the supplement was added to the quails from group 1, and the supplement was removed from the quails from group 2. It was observed that adding the supplement to the initial control group increased the weight of the eggs in 15 g, this is 261.3 g for the group to which the seaweed supplement was added and 261.8 gr for the group to which the supplement was removed.

While this invention has been described under the embodiments previously indicated, it could seems evident that other alternatives, modifications or variations could provide the same results; however, we have been able to establish that the selected seaweed, the process to obtain the supplement and the supplement itself are fundamentals for the success of the method. Consequently, the embodiments of the invention are intended to be illustrative, not limiting. Several changes can be made. Various changes can be made without departing from the spirit and scope of the invention as defined in the following claims. All patents, patent applications, scientific articles and other public documents known to the applicant constitute the state of the art have been properly cited in the present application.

The invention claimed is:

1. A process to prepare a dietary supplement for animals based on seaweed, wherein comprises the steps of:
   a. Selecting and washing the seaweed;
   b. Grinding the seaweed;
   c. Adding hot water and steam;
   d. Acid treatment of the seaweed;
   e. Washing the seaweed after the acid treatment of step d) and incubating with water;
   f. Adding whey during the water incubation period of step e);
   g. Applying an alkaline treatment with constant agitation;
   h. Adding hydrolyzed starch during the alkaline treatment of step g);
   i. Filtering to separate a solid phase from a liquid phase;
   j. Concentrating the liquid phase under vacuum;
   k. drying until the obtention of a powder product;
   l. Finally, pack and store the product obtained.

2. Process according to claim 1, wherein the seaweed selected in step a) comprise *Durvillaea* sp., *Macrocystis* sp., *Porphira* sp., *Ulva* sp., or combinations thereof, from which 1,000 kg are weighted and 30 minute washes are applied in a liquid:solid ratio of 2:1 to extract salts and impurities.

3. Process according to claim 1, wherein the seaweed from step b) is ground in a screw or knives mill until reaching a particle size between 0.5 and 1 cm.

4. Process according to claim 1, wherein during step c) for every 1,000 kg of the seaweed of step a), 2,000 L of hot water at a temperature between 50 to 60° C. are added with steam inclusion, mixed in a 5,000 L capacity tank.

5. Process according to claim 1, wherein during stage d) 50-70 L of apple vinegar is used for every 1,000 kg of initial seaweed and then 50-70 L of acetic acid are added for every 1,000 kg of the seaweed of step a).

6. Process of claim 1, wherein during step d) the acid treatment occurs at a pH of 2 to 6.5.

7. Process according to claim 1, wherein step e) comprises the incubation in water at a temperature of about 45-65° C. for about 90-120 minutes.

8. Process according to claim 1, wherein in step f) between 90 to 108 kg of whey are added for every 1,000 kg of the seaweed of step a).

9. Process according to claim 1, wherein during step g) between 45-50 kg of $K_2CO_3$ are used for every 1,000 kg of the seaweed of step a) and it is incubated between 70-80° C. for about 120-150 minutes.

10. Process according to claim 1, wherein in step g) the alkaline treatment occurs at a pH between 8.5 and 14.

11. Process according to claim 1, wherein in step h) 50 to 54 kg of hydrolyzed starch are added for every 1,000 kg of the seaweed of step a).

12. Process according to claim 1, wherein step i) comprises filtering the alkaline extract with a 250 microns filter.

13. Process according to claim 1, wherein step k) comprises drying the product by spray drying at an inlet temperature of about 150 to 170° C. and an outlet temperature of about 70 to 80° C.

\* \* \* \* \*